(12) United States Patent
Van Beek et al.

(10) Patent No.: US 11,278,355 B2
(45) Date of Patent: Mar. 22, 2022

(54) MODULAR FLUORO-NAVIGATION INSTRUMENT

(71) Applicant: SURGIVISIO, La Tronche (FR)

(72) Inventors: Laurence Van Beek, Saint Martin d'Uriage (FR); David Armand, Saint Egreve (FR); Arnaud Pierre, La Tronche (FR); Herve Collet, Chatenay (FR); Elie Fournier, Saint Martin le Vinoux (FR); Stephane Lavallee, Saint Martin d'Uriage (FR)

(73) Assignee: ECENTIAL ROBOTICS, Gieres (FR)

( * ) Notice: Subject to any disclaimer, the term of this patent is extended or adjusted under 35 U.S.C. 154(b) by 519 days.

(21) Appl. No.: 15/768,491

(22) PCT Filed: Oct. 14, 2016

(86) PCT No.: PCT/EP2016/074778
§ 371 (c)(1),
(2) Date: Apr. 13, 2018

(87) PCT Pub. No.: WO2017/064287
PCT Pub. Date: Apr. 20, 2017

(65) Prior Publication Data
US 2018/0280092 A1  Oct. 4, 2018

(30) Foreign Application Priority Data

Oct. 14, 2015 (EP) .................................... 15306636

(51) Int. Cl.
*A61B 34/20* (2016.01)
*A61B 90/00* (2016.01)
*A61B 90/96* (2016.01)

(52) U.S. Cl.
CPC .............. *A61B 34/20* (2016.02); *A61B 90/39* (2016.02); *A61B 90/96* (2016.02);
(Continued)

(58) Field of Classification Search
None
See application file for complete search history.

(56) References Cited

U.S. PATENT DOCUMENTS

| 5,935,128 A | * | 8/1999 | Carter | A61B 17/15 606/102 |
| 2006/0155189 A1 | * | 7/2006 | Lavallee | A61B 34/20 600/426 |

(Continued)

FOREIGN PATENT DOCUMENTS

| EP | 1779799 A1 | 5/2007 |
| EP | 2676627 A2 | 12/2013 |

(Continued)

OTHER PUBLICATIONS

International Search Report and Written Opinion received for PCT Patent Application No. PCT/EP2016/074778, dated Jan. 3, 2017, 11 pages.

(Continued)

*Primary Examiner* — Yi-Shan Yang
(74) *Attorney, Agent, or Firm* — Womble Bond Dickinson (US) LLP

(57) ABSTRACT

A modular fluoro-navigation instrument including a base made of a substantially radiotransparent material. The base is intended to be rigidly secured to a patient's bone and a tracker rigidly attachable to the base. The instrument has a registration phantom separate from the tracker which includes a plurality of radiopaque fiducials. The base and the registration phantom includes respective attachment members for reproducibly attaching the registration phantom to the base.

14 Claims, 11 Drawing Sheets

(52) U.S. Cl.
CPC .......... *A61B 2034/2051* (2016.02); *A61B 2034/2055* (2016.02); *A61B 2090/376* (2016.02); *A61B 2090/3966* (2016.02); *A61B 2090/3983* (2016.02)

(56) References Cited

U.S. PATENT DOCUMENTS

| | | | | |
|---|---|---|---|---|
| 2006/0173264 | A1* | 8/2006 | Jansen | A61B 34/20 600/407 |
| 2007/0122233 | A1* | 5/2007 | Maier | A61B 17/8866 403/200 |
| 2007/0253541 | A1* | 11/2007 | Sukovic | A61B 34/20 378/205 |
| 2011/0077695 | A1 | 3/2011 | Russell et al. | |
| 2012/0201421 | A1* | 8/2012 | Hartmann | A61B 6/5235 382/103 |
| 2012/0266898 | A1* | 10/2012 | Vogele | A61B 90/14 128/869 |
| 2015/0297314 | A1* | 10/2015 | Fowler | A61B 6/032 600/414 |
| 2016/0074129 | A1* | 3/2016 | Merritt | A61B 34/20 433/29 |
| 2018/0147021 | A2* | 5/2018 | Fleig | A61B 90/39 |

FOREIGN PATENT DOCUMENTS

| | | |
|---|---|---|
| EP | 2868277 A1 | 5/2015 |
| FR | 2941364 A1 | 7/2010 |
| WO | 2014/071969 A1 | 5/2014 |
| WO | 2015/090434 A1 | 6/2015 |

OTHER PUBLICATIONS

International Preliminary Report on Patentability received for PCT Patent Application No. PCT/EP2016/074778, dated Apr. 26, 2018, 8 pages.
European Search Report and Written Opinion received for EP Patent Application No. 15306636.0, dated Mar. 22, 2016, 8 pages.
Japanese Office Action received for JP Patent Application No. 2018-518701, dated Sep. 29, 2020, 10 pages (5 pages of English Translation and 5 pages of Original Document).

* cited by examiner

MODULAR FLUORO-NAVIGATION INSTRUMENT

FIELD OF THE INVENTION

The invention relates to a modular fluoro-navigation instrument.

BACKGROUND OF THE INVENTION

In surgery, X-ray fluoroscopy is frequently employed to guide surgical procedures. In particular, in orthopedic, spine and traumatology surgery, X-ray fluoroscopy is frequently employed to monitor fracture reduction, to insert instruments at precise locations and to position implants in one or several bone fragments. X-ray fluoroscopy can be a 2D image or a 3D image obtained from multiple 2D images using tomography reconstruction algorithms.

Fluoro-navigation is the application of real-time navigation on intraoperatively acquired fluoroscopic images to achieve the above-mentioned goals.

In view of carrying out fluoro-navigation, the tools used during the surgical intervention are equipped with a tracker, e.g. an optical, electromagnetic, ultrasonic, or inertial tracker which is followed by at least one localization system. Another tracker is mounted onto the patient and is also seen by the localization system.

Document FR 2 941 364 describes an apparatus for attaching an optical tracker to a patient. Said apparatus comprises a substantially flat radiotransparent body comprising a plurality of through bores. Pins are passed through said bores to secure percutaneously the body to a patient's bone. The apparatus further comprises, integral to the body, a protruding member intended to receive an optical tracker.

However, although the protruding member is located at a longitudinal end of the body in order to keep it away from the area of surgical intervention, the medical staff has to take care not to hit the optical tracker and/or the protruding member during the surgical intervention, which could displace the apparatus and thereby render the navigation data irrelevant.

In view of navigating surgical tools with respect to images acquired by the X-ray imaging device, it is necessary to know the position of the X-ray image detector with respect to the optical tracker fixed on the patient. To that end, in conventional systems, the X-ray imaging device is also equipped with an optical tracker that is seen by at least one camera of the localization system. However, since there may be a large distance between the optical tracker of the patient and the optical tracker of the X-ray imaging system, there is a risk that the field of view of the cameras of the localization system be obstructed by the medical staff during surgical intervention.

BRIEF DESCRIPTION OF THE INVENTION

A goal of the invention is to provide a fluoro-navigation instrument that overcomes the above-mentioned drawbacks of the known instruments. In particular, a goal of the invention is to design a minimally-invasive instrument for fluoro-navigation.

The invention relates to a modular fluoro-navigation instrument comprising:
a base made of a substantially radiotransparent material, the base being intended to be rigidly secured to a patient's bone;
a tracker rigidly attachable to the base;
characterized in that said instrument further comprises a registration phantom separate from the tracker comprising a plurality of radiopaque fiducials and in that the base and the registration phantom comprise respective fixation means for reproducibly attaching the registration phantom to the base.

By "separate from the tracker" is meant in the present text that the registration phantom is a distinct part from the tracker. This does not exclude that the registration phantom may be attached to the tracker (e.g. in the case the tracker is embedded into the base), but it must be removable from it.

Advantageously, the tracker comprises fixation means cooperating with said fixations means of the base for reproducibly attaching the tracker to the base.

According to an embodiment, the fixation means are configured so as to provide one or more determined positions for the tracker with respect to the base and a unique position for the registration phantom with respect to the base.

According to an embodiment, the tracker is an optical tracker.

According to an embodiment, the tracker is an electromagnetic tracker, optionally with inertial sensors.

According to an embodiment, the instrument further comprises a deformable material intended to be placed between the patient's skin and a support surface of the base facing the patient's skin, wherein said deformable material is capable of fitting the shape of the patient's skin and of rigidifying under an external solicitation.

According to an embodiment, the instrument further comprises an adhesive layer on a support surface of the base facing the patient's skin and intended to adhere to the patient's skin.

According to an embodiment, the base comprises a plurality of through holes.

Preferably, at least two of said through holes have non-parallel orientations.

The instrument may further comprise a plurality of pins adapted to be inserted in the through holes of the base so as to secure percutaneously the base to the patient's bone.

According to an embodiment, the instrument comprises a fixation system for rigidly attaching each of said pins to the base. Said fixation system comprises at least one of: a threaded section of the pin cooperating with a respective threaded section of the through hole; an element slidable along the pin capable of forcibly engaging a corresponding housing in the base; a pressure screw; a clamp; and a wedge element.

According to an embodiment, the base comprises at least one slot intended to pre-position the base onto at least one pin previously implanted into the patient's bone.

According to an embodiment, the instrument comprises a plurality a plurality of bases having different sizes and/or shapes, a single tracker and a single registration phantom capable of being reproducibly attached to each of said bases.

According to an embodiment, the instrument comprises a single base and a plurality of trackers and of registration phantoms capable of being reproducibly attached to said base and identified individually.

BRIEF DESCRIPTION OF THE DRAWINGS

Further features and advantages of the invention will be apparent from the description to follow, based on the appended drawings wherein.

DETAILED DESCRIPTION OF EMBODIMENTS OF THE INVENTION

The invention is carried out in a context of fluoro-navigation, i.e. in order to navigate a tool tracked by a localization system in an X-ray image acquired by a medical imaging system in the referential of the localization system.

Such navigation can be carried out in various types of surgical interventions carried out onto a patient's bone, including but not limited to: implantation of orthopaedic implants such as pedicular screws, insertion of surgical instrumentation such as spine trocar to be used in vertebroplasty procedure, implantation of various orthopaedic implants such as hip, knee or shoulder implants, reduction and fixation of fractures during traumatologic procedures.

The medical imaging system comprises at least one X-ray source and at least one X-ray detector. For example, the medical imaging system can be a C-arm, an O-arm or a scanner.

The medical imaging system is motorized on at least one movement which contributes to generate a 3D acquisition trajectory, i.e. each movement of the system according to a degree of freedom is generated by a respective motor. Each motor is associated to an encoder allowing knowing, at any time, the relative position of the medical imaging system with respect to a reference position. When a 2D image is acquired, the corresponding position of the imaging system is recorded. Thus, each 2D image is recorded in the referential of the imaging system.

In general, several images are acquired at the beginning of the surgical intervention and said images are used for reconstruction of a 3D volume or 3D image. Besides, during the surgical intervention, one or more extra 2D or 3D images may be acquired to check progress of the intervention.

The fluoro-navigation further requires a computer comprising at least one processor to carry out algorithm allowing registering the 3D volume with a given referential.

Figure 1:
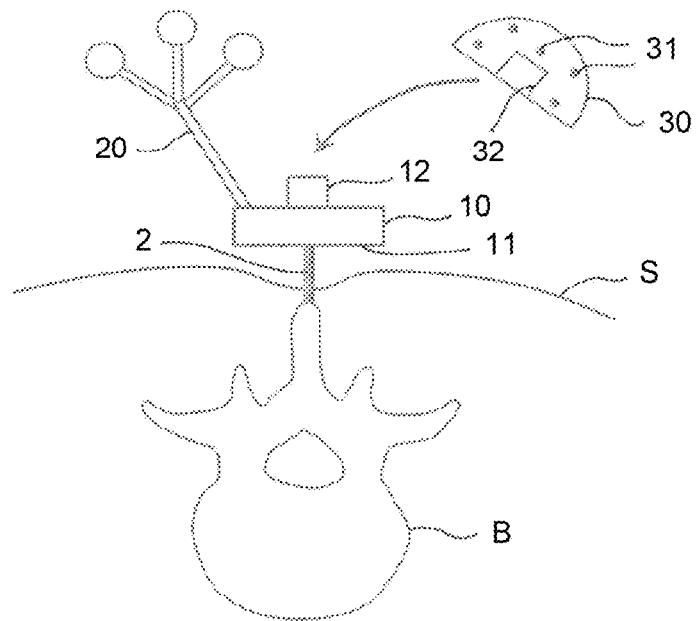
FIG. 1 schematically illustrates a modular instrument according to an embodiment of the invention, wherein the base is directly fixed to the patient's bone.

FIG. 1 shows an embodiment of a modular instrument 1.

The instrument 1 comprises a base 10 made of a radiotransparent material, e.g. plastics.

The base 10 is intended to be rigidly fixed to a patient's bone B.

Figure 2:
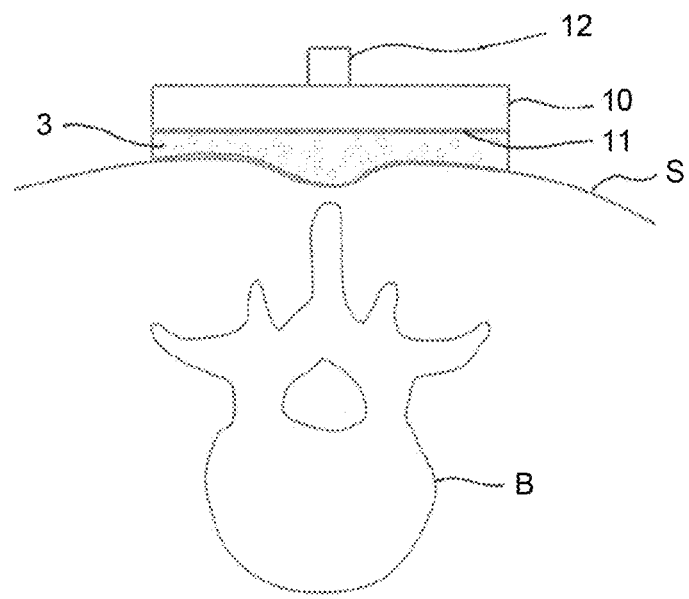
FIG. 2 schematically illustrates a modular instrument according to another embodiment of the invention, wherein the base is indirectly fixed to the patient's bone.
Figure 3:
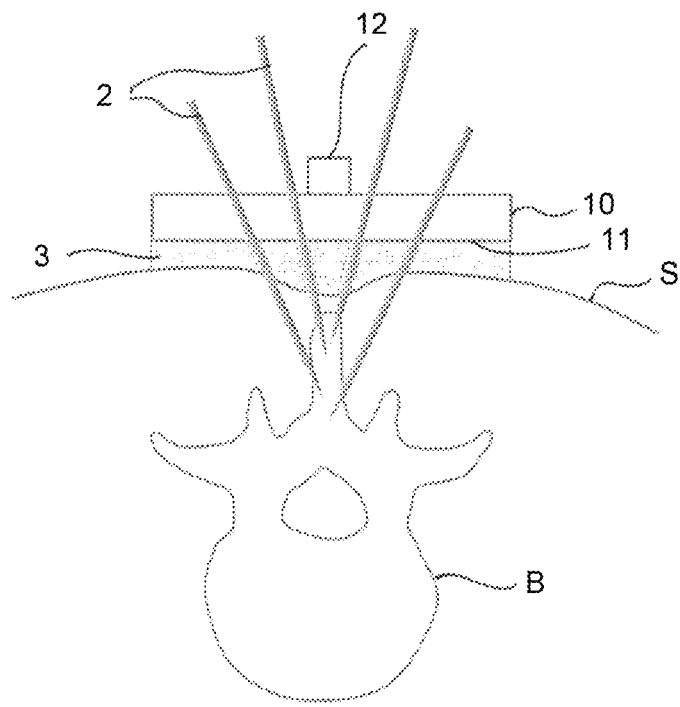
FIG. 3 schematically illustrates a modular instrument according to another embodiment of the invention, wherein the base is fixed directly and indirectly to the bone.

By "rigidly fixed" is meant in the present text that the base does not move with respect to the bone during the surgical intervention. The fixation may be either direct (e.g., as shown in FIG. 1, using at least one percutaneous pin 2, needle, broach or screw implanted into the bone in a minimally invasive way) or indirect (i.e. using attachment means external to the bone, such as an adhesive tape on the skin close to the bone, straps, etc. to immobilize the base with respect to the bone without passing through the patient's skin). For example, as shown in FIG. 2, a deformable material 3 is interposed between the base 10 and the skin S. Said deformable material can be silicon, thermodurcissable foam, a bag containing microbeads that can be rigidified under vacuum, or an adhesive tape. The material 3 fitting to the body part shape provides some stability to the base relative to the bone, especially in non-flat regions. Adhesion between the material 3 and the skin and the base can be obtained either by adhesive properties of the material or by external means such as straps, adhesive tape surrounding the base. The indirect fixation is particularly adapted when there is only a small thickness of soft tissues between the bone and the base, since this situation is considered to provide sufficient rigidity to prevent any movement of the base relative to the bone. For example, indirect fixation can be used when the bone pertains to a patient's finger, wrist, foot, etc. Such an indirect fixation has the advantage of being non-invasive. If required, direct and indirect fixation can be combined. For example, in the embodiment of FIG. 3, the base 10 is linked to the skin S via a deformable material 3 that fits to the body part shape and at least one percutaneous pin 2, broach, needle or screw further secures the base 10 to the bone B. If the intervention is performed on several bones, or several bone fragments, it is possible to use multiple bases, one base per bone or bone fragment. In a preferred embodiment, such as a complex articulation of several bones, a deformable material that can become rigid is first used to fix the individual bones or bone fragments together: conventional plaster, thermo-deformable material, poach of micro spheres with vacuum, etc. and the basis is then fixed to this deformable material once it is rigid.

The base 10 has a support surface 11 intended to face the bone (the patient's skin or tissues surrounding the bone may be located between the base and the bone). Said support surface 11 may have any shape (e.g. circular, rectangular, etc.) and size suitable for the intended application, in particular depending on the shape and size of the body part to which the base has to be fixed. For example, for spine surgery, the base preferably has an elongated shape so as to be fixed to at least two or three adjacent vertebrae, whereas for shoulder surgery the base is rather circular with an oblong extension so as to be fixed to the acromion. The support surface 11 may extend in a plane or may be either concave or convex, rigid or deformable.

As will be shown in more detail below, the fixation is preferably designed so as to avoid any contact between the support surface 11 and the skin S, in order to avoid hurting the patient and in particular to avoid creating bed sores during the surgical intervention that may last a few hours. Thus, in a preferred embodiment, the support surface 11 is advantageously maintained at a certain distance from the patient's skin.

The base advantageously has a generally a height of less than 20 mm. In this way, the base is very compact and protrudes only to a limited extent from the patient's skin. Thus, it is quite unlikely that the medical staff unintentionally hits the base and thus displaces it relative to the bone during the surgical intervention.

The base 10 has a tracker 20 rigidly coupled thereto. Said coupling can be permanent (the tracker being integral with the base or irreversibly fixed to the base) or temporary (the tracker being detachable from the base).

According to a preferred embodiment, the tracker can be detached from the base when no tracking is required, thus offering a temporary coupling. This reduces the risk of having the tracker hit by the medical staff and thus causing a displacement of the base relative to the bone. It also saves operating space when the tracker is not needed.

In the case of said temporary coupling, the base and tracker have cooperating fixation means that allow detaching and attaching the tracker in a reproducible way (i.e. always in a same known position and orientation relative to the base).

According to an embodiment, the tracker is an optical tracker (either active or passive). For example, in the embodiment shown in FIG. 1, the tracker comprises a plurality of reflective balls having a known relative position.

Figure 4A:
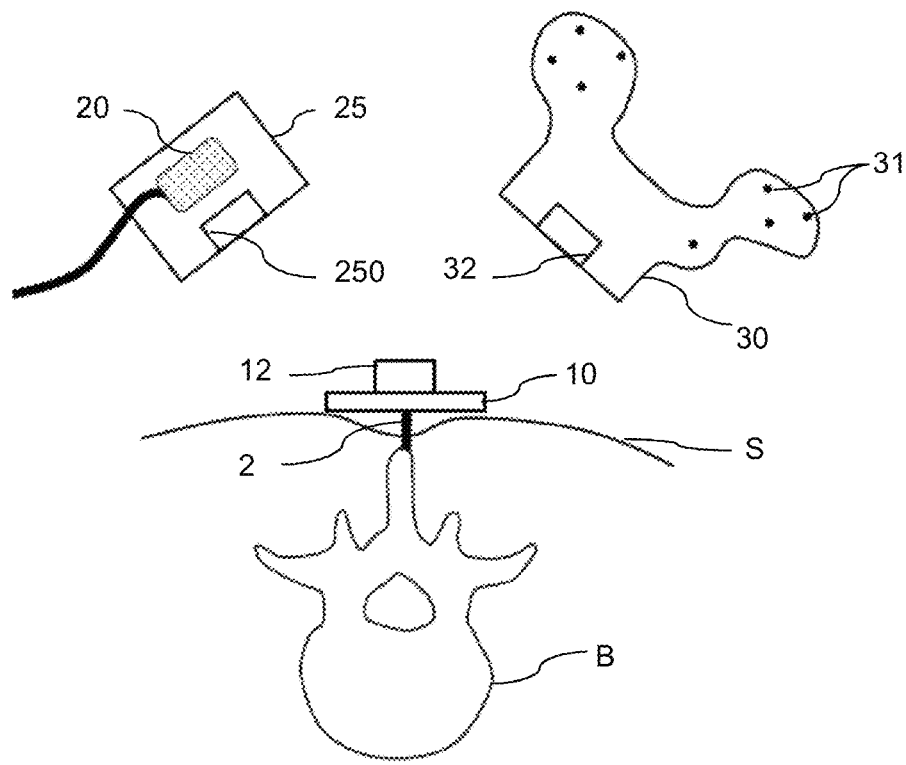
FIGS. 4A and 4B schematically illustrate a modular instrument according to embodiments of the invention wherein the tracker is an electromagnetic tracker.
Figure 4B:
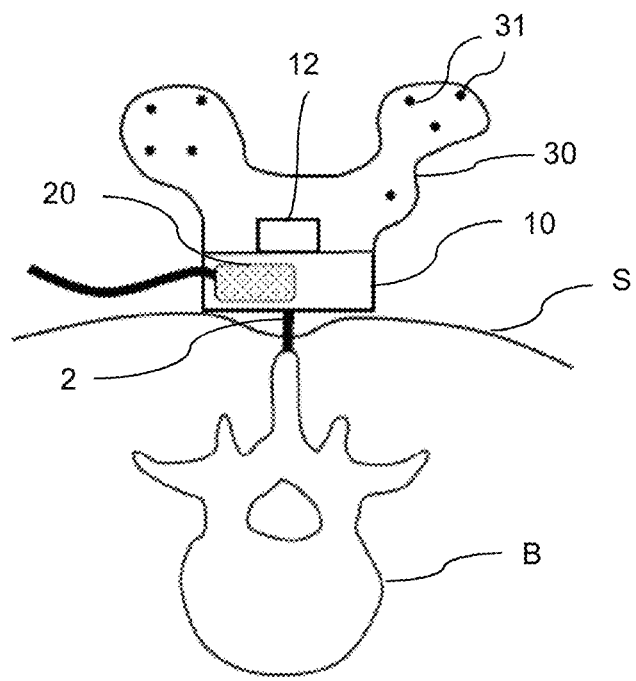

According to another embodiment, the tracker is an electromagnetic tracker. An electromagnetic tracker has the advantage of being more compact than an optical tracker. For example, in the embodiment shown in FIG. 4A, the tracker 20 is embedded in a support 25 which can be attached to the base 10 with the reproducible fixation means 12, 250. In an alternative embodiment shown in FIG. 4B, the tracker 20 is lodged in a recess of the base 10 and thus does not protrude from the base. The tracker 20 may be removable or not from the base 10. In a preferred embodiment, the electromagnetic tracker contains inertial sensors that can be used to detect the presence of artefacts.

The invention is not limited to a specific tracking technology and the skilled person can adapt the described embodiments to the selected technology.

The instrument 1 further comprises a registration phantom 30 intended to be rigidly attached to the base 10. The registration phantom 30 is made of a radiotransparent material and comprises a plurality of radiopaque fiducials 31 having a known shape and size (e.g. balls or pins) arranged in a known position.

When a 2D image is acquired with the medical imaging system, the radiopaque fiducials are visible in the 2D image. Since the shape, size and arrangement of the radiopaque fiducials is known, the image can be determined in the referential of the calibration phantom and the 3D reconstruction can be carried out based on the position of the radiopaque fiducials in each 2D image. It is also possible to perform a 3D image reconstruction directly without using the fiducials and then to detect the fiducials directly in the reconstructed 3D image.

Since the registration phantom 30 is not required during the whole surgical intervention but only at specific times when registration of the images acquired by the medical imaging system has to be carried out, the registration phantom 30 is detachable from the base 10.

To that end, the base 10 and the registration phantom 30 have cooperating fixation means 12, 32 that allow attaching the registration phantom in a reproducible way (i.e. always in a same known position and orientation relative to the base). This allows saving operating space when the phantom is not needed.

The registration phantom 30 may have any shape and size suitable for the intended application. In particular, since the registration phantom 30 is only attached to the base when it is required for image registration, the registration phantom 30 can have a greater size than the base. In this way, it is possible to have the radiopaque balls located at a greater distance from each other and thus improve the accuracy of the registration.

According to an embodiment, the fixation means comprise at least one finger 12 protruding to the surface of the base opposite to the support surface 11 and at least one respective complementary opening 32 in the registration phantom 30. However, this embodiment is not limitative and the skilled person could design another type of reproducible fixation without departing from the scope of the present invention.

Figure 5:
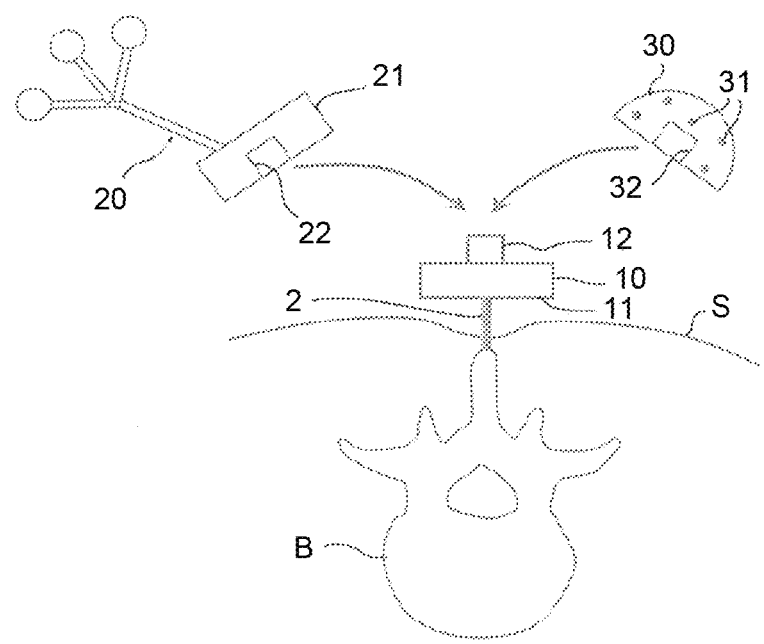
FIG. 5 schematically illustrates a modular instrument according to an embodiment of the invention, wherein the base comprises a reproducible fixation common to the tracker and the registration phantom.

Preferably, as shown in FIG. 5, the reproducible fixation for the registration phantom 30 is the same as for the tracker 20 (when the tracker is detachable from the base). In this way, the design of the base is as simple as possible and no space is lost by providing two distinct fixations areas on the base.

Advantageously, the registration phantom and, if applicable, the tracker, is maintained onto the base using magnetic force thanks to a magnet arranged in the base. Thus, attachment and removal of the registration phantom and, if applicable, the tracker, can be made easily without requiring any tool. This magnetic fixation has also the advantage of being detached automatically if a certain level of forces are exerted on the part mounted to the base, which avoids to damage or displace the relative position and fixation of the base with respect to the bone.

Figure 6A:
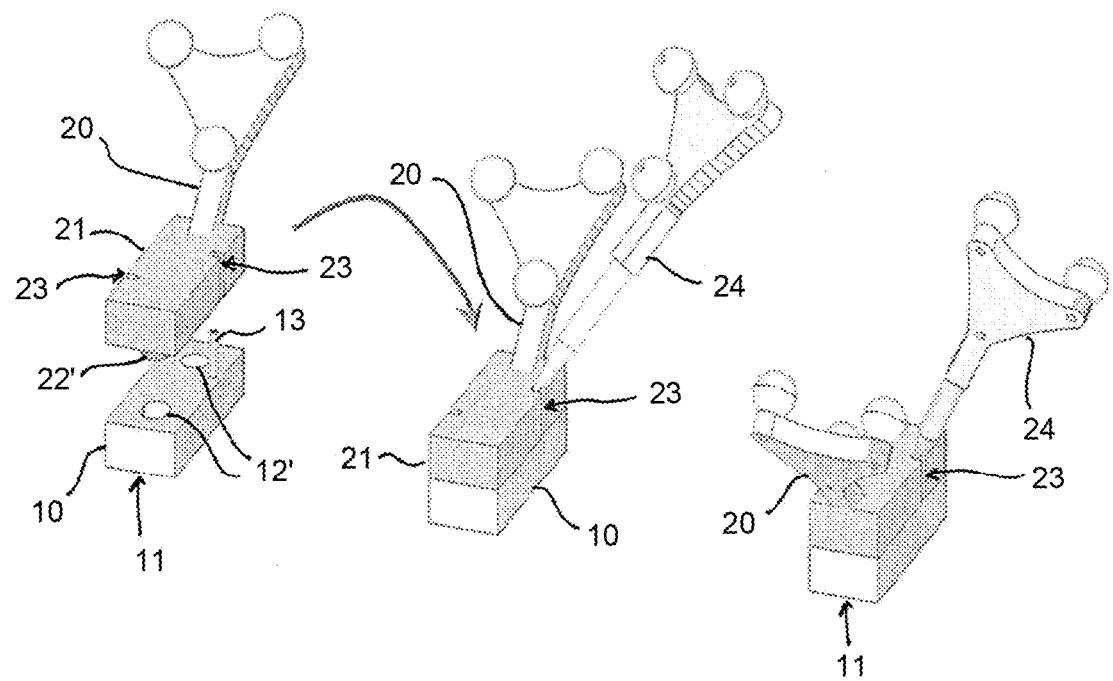
FIGS. 6A and 6B schematically illustrate a modular instrument according to an embodiment of the invention, wherein the tracker has a symmetric reproducible fixation to the base whereas the registration phantom has a unique reproducible fixation to the base.
Figure 6B:
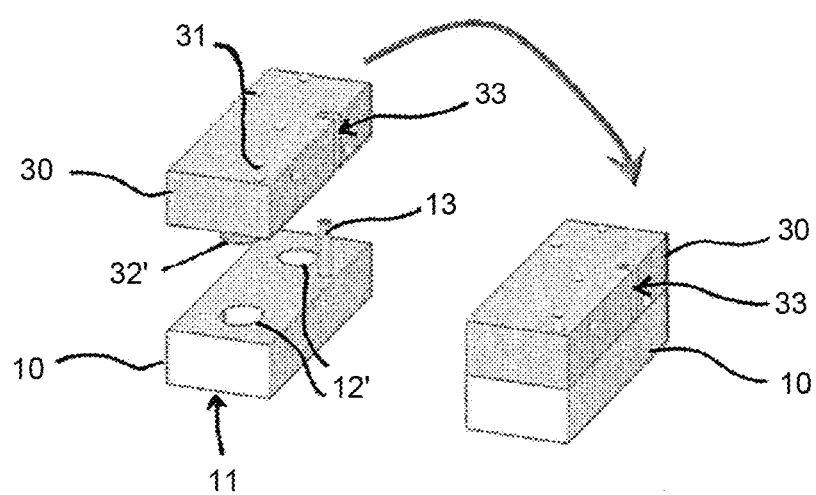

According to an embodiment illustrated in FIG. 6A, the tracker can be removably fixed to the base by a reproducible fixation that allows one or more determined possible positions of the tracker with respect to the base. For example, the tracker 20 comprises a support 21 comprising two cylindrical protrusions 22' engaging respective cylindrical openings 12' in the surface opposite to the support surface 11 of the base. The base further comprises a finger 13 extending from the surface opposite to the support surface 11. The support 21 of the tracker comprises two passages 23 arranged such that the finger 13 engages one passage 23 when the tracker is fixed onto the base in a first possible position (see middle of FIG. 6A) and into the other passage when the tracker is fixed onto the base in the second possible position (see right of FIG. 6A). As will be explained in more detail below, the top of the finger 13 serves as a reference point to determine the real position of the tracker relative to the base using a tracked tool 24. Such a symmetric fixation is advantageous in that it provides more flexibility to the medical staff to position the tracker in the operating space, in particular depending on the position of a localization camera that is used for navigation. It is also advantageous to release the constraint linked to positioning of the base onto the bone at the beginning of the surgical procedure; the medical staff can focus on positioning of the base relative to the bone choosing positioning direction depending only on bone quality of bone fixation and afterwards position the tracker onto base depending on the suitable operating set-up. On the other hand, as shown in FIG. 6B, the reproducible fixation of the registration phantom 30 to the base 10 is unique. To that end, the registration phantom 30 comprises two cylindrical protrusions 32' cooperating with the cylindrical openings 12' in the surface opposite to the support surface 11 of the base but only one passage 33 for the finger 13. In the embodiment described above, the two possible positions of the tracker relative to the base are symmetric. However, there may be more than two possible positions for the tracker. For example, for a base having a substantially circular shape (not shown), the reproducible fixation could comprise a conical protrusion in the center of the base and fingers arranged at given angular positions to define the possible positions of the tracker.

According to another embodiment (not shown), the reference point may be on the tracker.

Figure 7:
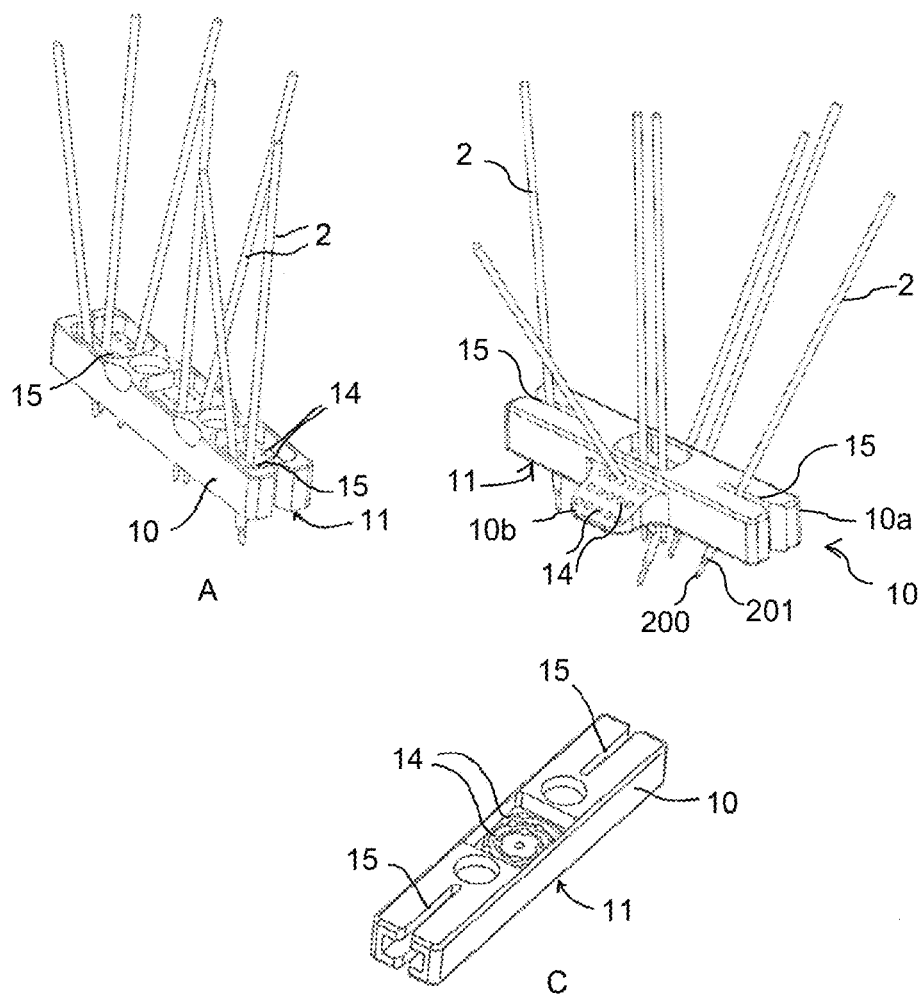
FIG. 7 illustrates various embodiments of a base according to the invention intended to be fixed to the bone by pins.

FIG. 7 shows three embodiments (A) to (C) of the base 10 intended to be fixed to the bone by at least one percutaneous pin 2, screw, needle or broach. In the following description, the term "pin" will be used to designate any elongated percutaneous device for fixing the base to the bone, including a screw, a broach, a needle. In general, such a pin has a pointed tip 200 so as to allow perforation of the skin and implantation into the bone, and a diameter comprised between 0.5 and 8 mm.

According to a preferred embodiment, the pin 2 comprises a shoulder 201 located at a limited distance (a few millimeters, e.g. 4 mm) from the tip 200. The shoulder 201 forms an abutment that prevents the practitioner from inserting the pin into the bone further from said limited distance. This is a safety means that avoids damaging the bone or surrounding tissues (e.g. spine canal, vascular structures) in case the pin is not inserted exactly in the desired region of the bone. In addition, the practitioner may also control that the pin is fully implanted into the bone by sensing that the shoulder contacts the bone.

The base comprises a plurality of through holes 14 for passing a respective pin 2. Each through hole has a cylindrical shape with a diameter complementary to the diameter of the pin. Each through hole 14 has a sufficient height so as to guide the pin and avoid any pivoting of the pin relative to the base. The number of through holes is advantageously high so as to provide a large choice for practitioner to select the most suitable holes though for receiving pins so as to provide an optimal fixation to the bone. At least three pins are required to prevent any rotation of the base relative to the bone. Preferably, a greater number of pins is used in order to create multi-constraint that allow preventing any movement of the base.

Figure 8:
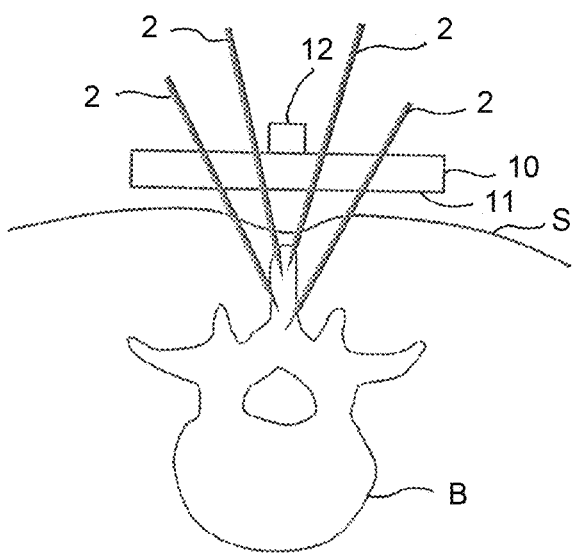
FIG. 8 schematically illustrates a base maintained at a certain distance of the skin using a plurality of pins creating a multi-constraints fixation.

Advantageously, the through holes 14 are not parallel to each other, so as to provide a more stable fixation of the base (the multiplicity of the angles of the pins creating a multi-constraints situation). In addition, non-parallel pins allow maintaining a distance between the base and the skin (see FIG. 8), which limits mechanical constraints applied to the underlying tissues.

The pins may comprise a notch (not shown) allowing each pin to be broken once it has been implanted into the bone and secured to the base. In this way, the portion of the pins extending above the base can be removed and thus do not obstruct the operating space. This also makes the fixation of the phantom and tracker easy. Otherwise, the pin may be cut by suitable pliers with sharp edges.

In the embodiment (A) of FIG. 7, the base 10 has a substantially rectangular shape with several regions containing through holes 14. Advantageously, the regions wherein the through holes are arranged have a limited thickness defining the required height of the through holes, and said regions are surrounded by a peripheral flange to increase the rigidity of the base. If the pin is broken or cut after being fixed to the bone and secured to the base, the cut is preferably located within said peripheral flange so as not to protrude from the base.

In the embodiment (B) of FIG. 7, the base has a substantially rectangular central portion 10a with two wings 10b extending from the longitudinal sides of the portion 10a. Each wing 10b is advantageously inclined with respect to the support surface 11 and comprises a plurality of through holes 14 also inclined with the support surface 11. The wings 10b offer an improved ease of use due to the increased accessibility of the through holes. The central portion 10a can also comprise a plurality of through holes.

In the embodiments (A), (B) and (C) of FIG. 7, the base 10 further comprises at least one longitudinal slot 15 (preferably two) extending inwardly from a respective edge of the base. Each slot extends through the height of the base until the support surface 11. Said slot allows a pre-positioning of the base relative to the bone. First, the practitioner can attach two pins 2 to the bone, the pins not being parallel to each other. The position of said pins is advantageously chosen so as to ensure a good fixation to the bone; in particular, the practitioner selects optimal bone regions to implant the tip of the pins. Then, the practitioner can position the base such that each pre-positioned pin 2 enters a respective slot 15. He then slides the base along the pins 2 until reaching the final position of the base wherein the base 10 is wedged onto the pins 2. For example, the practitioner can manually sense the shape of the underlying bone and determine whether the base is correctly placed relative to the parts of the bone to which it can be optimally fixed. Then, additional pins 2 can be passed through the through holes 14 in order to rigidly fix the base to the bone.

In the embodiment (C) of FIG. 7, the holes 14 are further arranged along concentric circles in a central portion of the base. A central through hole can also be arranged at the center of said circles. Advantageously, the through holes of a circle all converge towards a common point that is different from one circle to another one.

Of course, the embodiments (A) to (C) are not limitative and the skilled person could define another arrangement for the through holes 14, and, if any, the slots 15; in particular, features of these embodiments could be combined without departing from the scope of the present invention.

The modular instrument may be presented as a kit containing several bases of different sizes and/or shape but a single tracker and a single registration phantom. This variety of bases allows the practitioner selecting the most suitable base depending on the body part to be treated and/or the specificities of the patient. For example, for an obese patient, the angles of the through holes may be required to be greater than for a slim patient. Inversely the modular instrument may be presented as a kit containing several registration phantoms and/or trackers of different sizes and/or shapes but a single base. According to another embodiment, the kit comprises a plurality of bases having different sizes and/or shapes and a plurality of trackers and of registration phantoms of different sizes and/or shapes capable of being reproducibly attached to each of said bases. This variety allows the practitioner selecting the suitable instrument depending on the surgical procedure he wants to realize. For example, for a scoliotic patient whose vertebrae shall be largely deformed, the orientation of reflective spheres regarding the reproducible face of the tracker and its overall external dimensions may be required to be changed relative to a standard patient.

When the correct position of the base relative to the bone has been determined and the pins have been passed into the through holes (and slot(s) if appropriate) and implanted into the bone, the practitioner secures the pins to the base.

Figure 9:
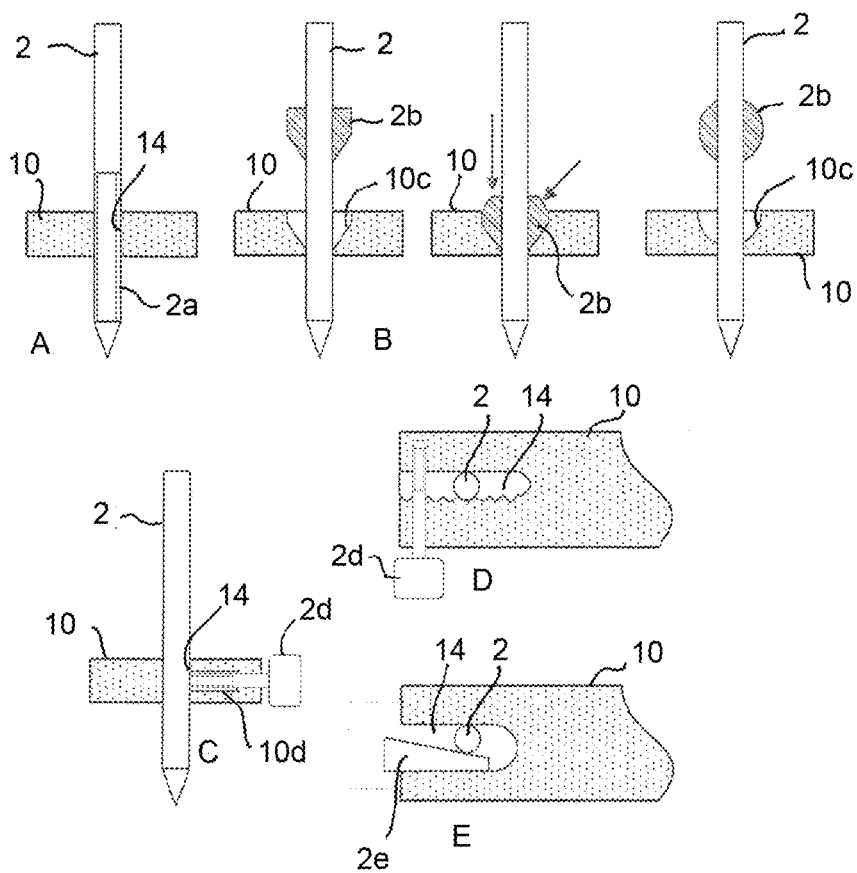
FIG. 9 schematically illustrates various ways of securing the pins to the base.

FIG. 9 illustrates various ways of securing a pin to the base.

In embodiment (A), the pin 2 has a threaded end that cooperates with a threaded section of the through hole 14.

In embodiment (B), the pin 2 is provided with an element 2b slidingly arranged around the pin. Once the pin is implanted into the bone (left), the practitioner slides the element 2b until engaging a corresponding housing 10c in the base. Then, via impaction (and possible deformation of the external shape of the element), he secures the element 2b in the housing 10c (middle). The element can have a wedge shape (left and middle) or a round shape (right).

In embodiment (C), the base is provided with a threaded hole 10d extending in a direction substantially perpendicular to the direction of the through hole and leading into said through hole. Thus, when the pin has been implanted into the bone, a pressure screw 2d can be screwed into the hole 10d until contacting and pressuring the pin 2.

In embodiment (D), the region of the base surrounding the trough hole can be deformable so as to form a clamp for the pin 2 and pressure can be applied to the clamp one the pin has been implanted into the bone by a pressure screw 2d, a deformable clip or any other suitable means. This embodiment is also suitable to secure a pin into a slot 15 as shown in FIGS. 7 (B) and (C).

In embodiment (E), the through hole 14 is in the form of a slot extending from an external side of the base and having a greater width than the diameter of the pin 2. Once the pin has been implanted into the bone, a wedge element 2e is inserted into the hole and forcibly maintains the pin against a wall of the through hole. This embodiment is also suitable to secure a pin into a slot 15 as shown in FIGS. 7 (B) and (C).

In another embodiment, the multiplicity of pins oriented with various angles (such as in FIG. 8) allows securing the base without requiring any external means.

Figure 10:
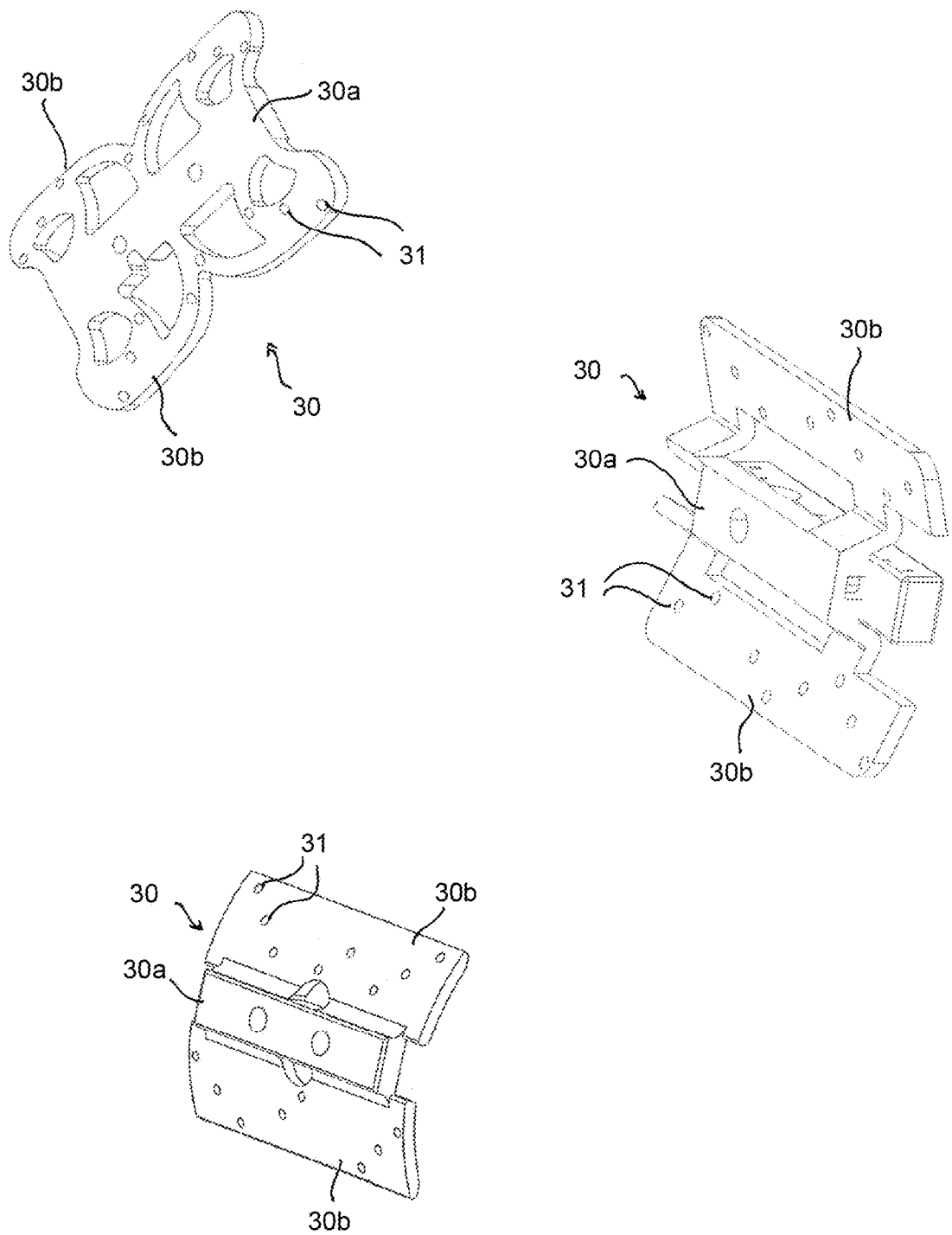
FIG. 10 illustrates various embodiments of the registration phantom.

FIG. 10 illustrates various embodiments of the registration phantom 30. Advantageously, the registration phantom 30 comprises a central portion that is intended to be fixed to the base and two lateral wings 30b extending on either side of said central portion 30a. Preferably, the lateral wings are integral with the central portion. Depending on the application, the base and lateral wings may substantially extend in a plane; otherwise, the lateral wings may be inclined with respect to the central portion. In another embodiment, the wings may extend above the central portion.

Figure 11:
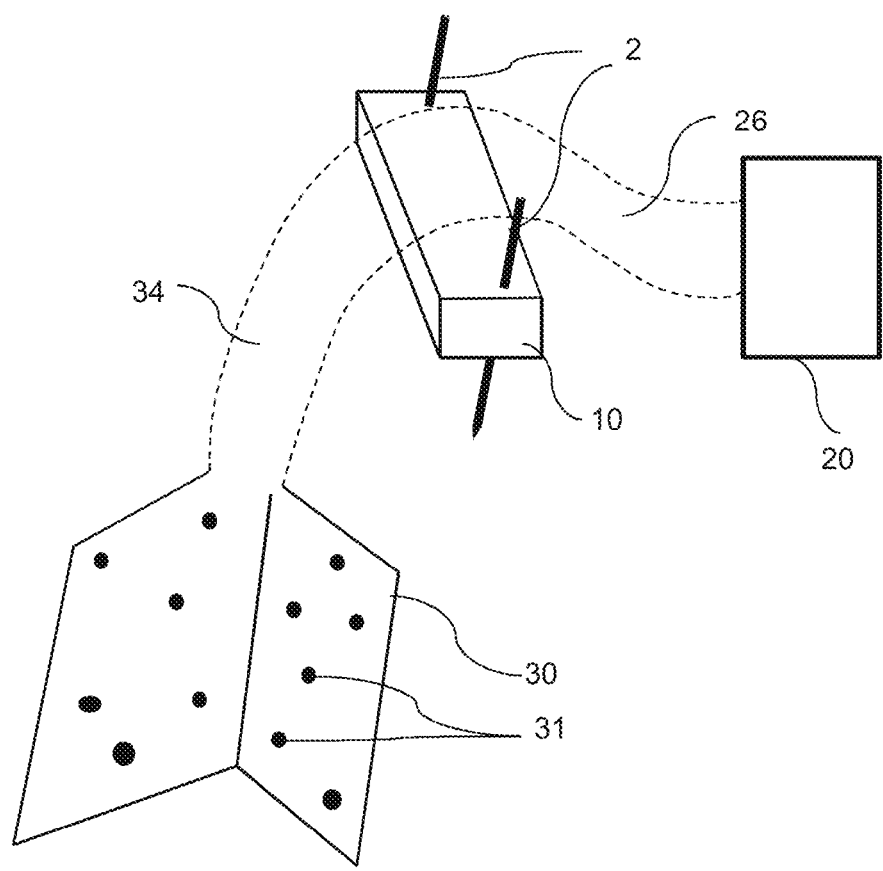
FIG. 11 schematically illustrates an embodiment of the registration phantom and tracker attached to the base.

FIG. 11 shows a schematic embodiment of the tracker 20 and the registration phantom 30. While the base 10 is advantageously compact in order to have an optimal stability relative to the bone (in the illustration, the base is fixed to the bone by two pins 2, but it could also be fixed by any direct or indirect method described above). By contrast, the tracker 20 and/or the registration phantom 30 comprise a respective elongated member 26, 34 that allows placing the tracker and/or the registration phantom in an offset position relative to the base. The elongated members 26, 34 are represented by dashed lines, their shape and dimension being dependent from the intended surgical application. These elongated members allow optimizing the position of the tracker and/or the base while maintaining the base in an optimal position in terms of osseous fixation and accessibility. For example, the elongated member 34 may allow placing the registration near the center of the imaged region, in order to have the radiopaque fiducials 31 in an optimal position for the reconstruction of the 3D image. In case of an optical tracker, the elongated member 26 may allow placing the tracker in an optimal position in the field of view of the localization camera. The elongated member 26 may allow placing the tracker away from the intervention site in order to free space for the practitioner. In case of an electromagnetic tracker, the elongated member 26 may allow placing the tracker near the intervention site, in order to provide a more precise localization.

The modular instrument can be used according the following protocols.

Protocol n°1

Figure 12:
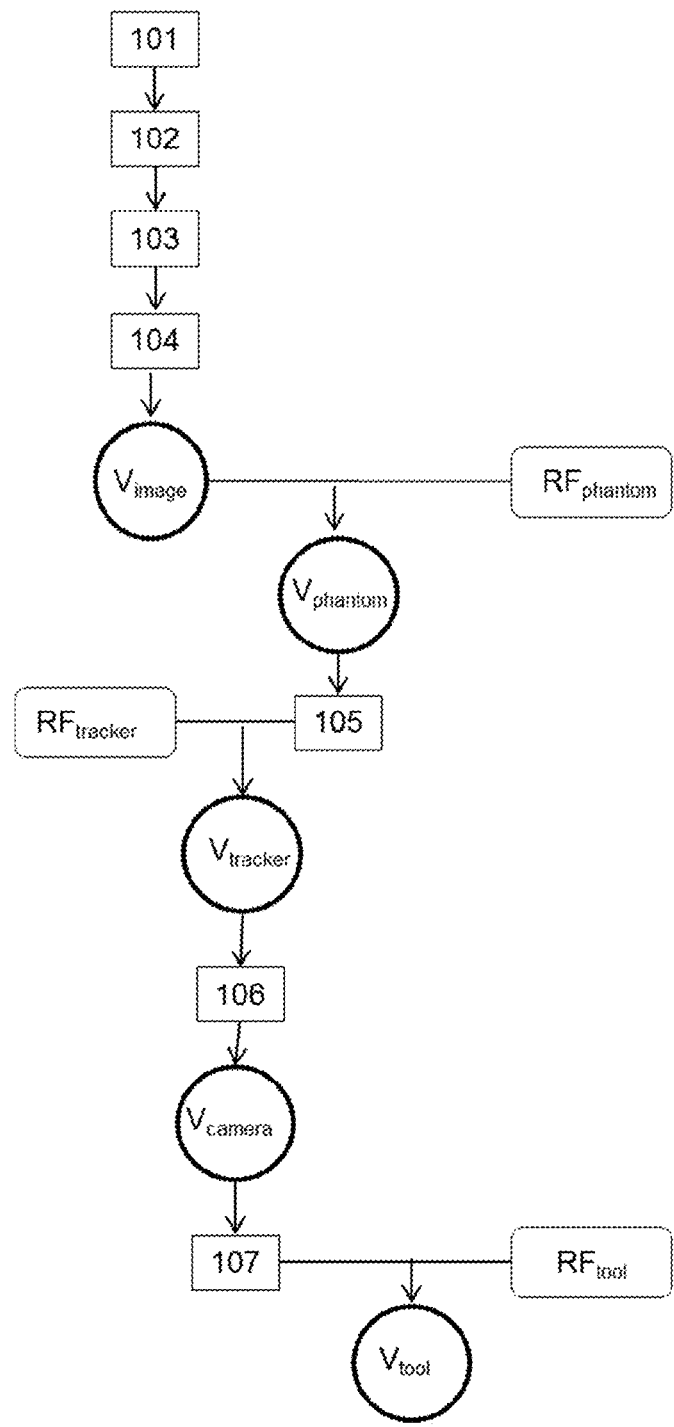
FIG. 12 is a flowchart representing a protocol that may be implemented during a surgical intervention using an instrument.

FIG. 12 is a flowchart representing a protocol that may be implemented during a surgical intervention using an instrument as described above.

In step 101, the base is rigidly attached to the bone, either in a direct or an indirect way.

In step 102, the registration phantom is attached to the base using the reproducible fixation means.

In step 103, the motorized medical imaging system acquires images of the patient in the region of the bone.

In step 104, a 3D reconstruction algorithm is implemented by the computer so as to generate a 3D volume $V_{image}$ which is defined in the referential of the imaging system. 3D reconstruction is known per se and thus will not be described in detail here.

On the other hand, a registration algorithm is implemented by the computer so as to generate the 3D volume in the referential of the registration phantom, based on the known phantom dimensions (noted $RF_{phantom}$) that are stored in a memory of the computer or that may be downloaded from another system. This 3D volume is referred to as $V_{phantom}$.

In step 105, the registration phantom is removed from the base and the tracker is attached to the base using the reproducible fixation (unless the tracker is permanently attached to the base, in which case the tracker is present during all the protocol).

Since the tracker has known position and fixation relative to the base (noted $RF_{tracker}$), the computer implements an algorithm to generate the above-mentioned 3D volume in the referential of the tracker. This 3D volume is referred to as $V_{tracker}$.

In step 106, a localization camera is installed in the vicinity of the patient such that the tracker is in the field of view of the camera.

The computer implements an algorithm to generate the 3D volume in the referential of the camera. This 3D volume is referred to as $V_{camera}$.

In step 107, a tracked tool is introduced in the operating field in order to carry out the surgical intervention. The tool is also in the field of view of the localization camera, such that the position of the tool tip (noted $RF_{tool}$) is known at each time. The position of the tool tip may be stored in a memory of the computer or may be downloaded from another system.

Then, the computer implements an algorithm so as to generate the 3D volume in the referential of the tracked tool. This 3D volume is referred to as $V_{tool}$. Thus, navigation of the tool in the volume $V_{tool}$ can be carried out.

Protocol n°2

Figure 13:
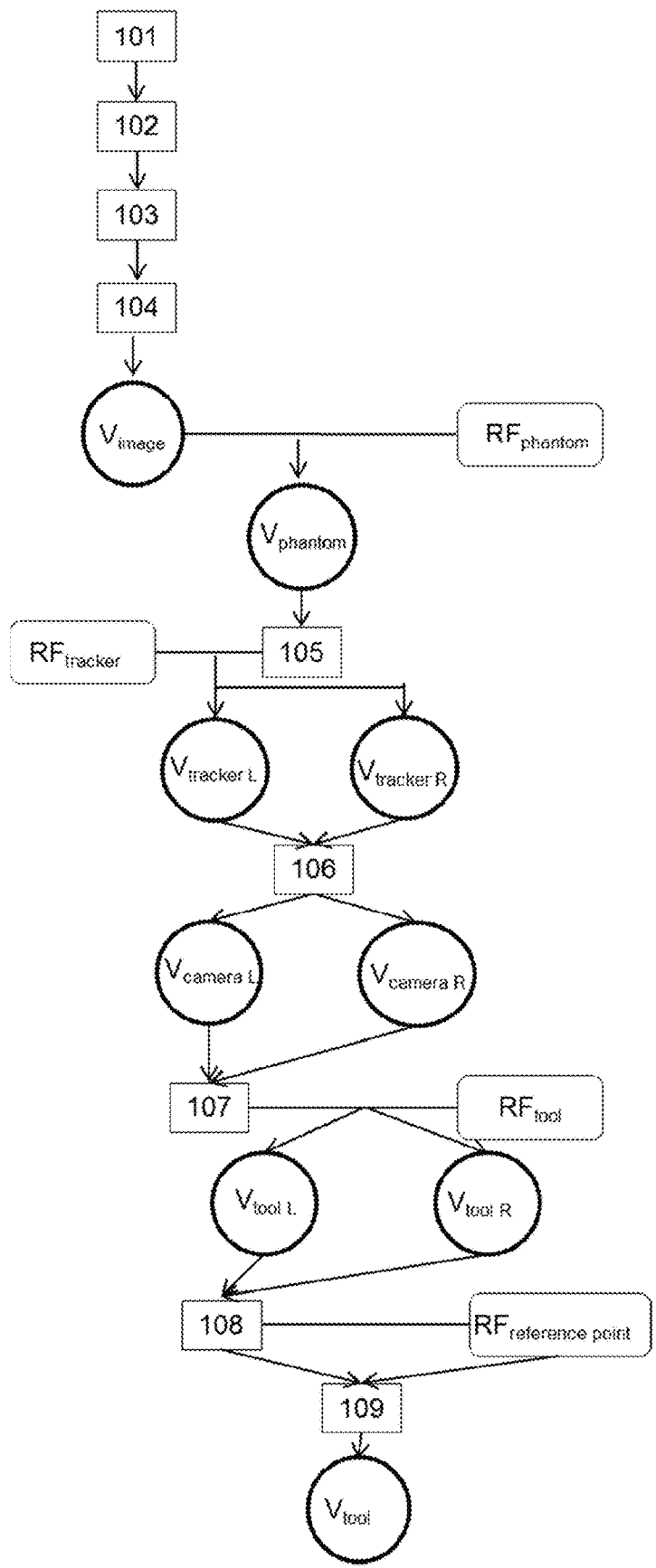
FIG. 13 is a flowchart representing an alternative protocol that may be implemented in the case of a symmetric fixation of the tracker relative to the base.

FIG. 13 is a flowchart representing an alternative protocol that may be implemented in the case of a symmetric fixation of the tracker relative to the base.

The steps that have the same reference as in FIG. 12 correspond to the same steps as in the first protocol and will thus not be described again.

In step 105, the tracker is attached to the base in any one of the two possible symmetric positions. Advantageously, the tracker is positioned in the position corresponding to an optimal field of view for the localization camera to be used for navigation or as a direct consequence of camera set-up in the operating room.

Since the tracker has known position and fixation relative to the base, the computer implements an algorithm to generate a first 3D volume in the referential of the tracker assuming that the tracker is in the first position (e.g. left) and a second 3D volume in the referential of the tracker assuming that the tracker is in the second position (e.g. right). These 3D volumes are referred to as $V_{tracker\ L}$ and $V_{tracker\ R}$, respectively.

In step 106, the localization camera is installed in the vicinity of the patient such that the tracker is in the field of view of the camera.

The computer implements an algorithm to generate each of above-mentioned 3D volumes in the referential of the camera. These 3D volumes are referred to as $V_{camera\ L}$ and $V_{camera\ R}$, respectively.

In step 107, a tracked tool is introduced in the operating field in order to carry out the surgical intervention. The tool is also in the field of view of the localization camera, such that the position of the tool tip is known at each time. The position of the tool tip may be stored in a memory of the computer or may be downloaded from another system.

Then, the computer implements an algorithm so as to generate each of the above-mentioned 3D volumes in the referential of the tracked tool. These 3D volumes are referred to as $V_{tool\ L}$ and $V_{tool\ R}$, respectively.

In order to determine the real position of the tracker relative to the base, thus choose between $V_{tool\ L}$ or $V_{tool\ R}$, a tracked tool (which may be the same as the above-mentioned tool or another one) is positioned so as to contact a reference point on the base with its tip (step 108).

Since the position of said reference point (noted $RF_{reference\ point}$) is known, the computer implements an algorithm to compare the position of the reference point and the position of the tool tip and to select the referential (L or R) accordingly (step 109).

Thus, navigation of the tool in the appropriate referential can be carried out.

The above protocols refer to reference features such as tool tip, reference point, phantom dimensions, tracker dimensions that are known at each time.

In a preferred embodiment, these reference features may be stored in a memory of the computer.

In another embodiment, the reference features may be generated by a part of the system, as calibrators for instruments and/or calibration algorithm of the localization system itself. This embodiment suits particularly the use of re-usable instruments.

Figure 14:
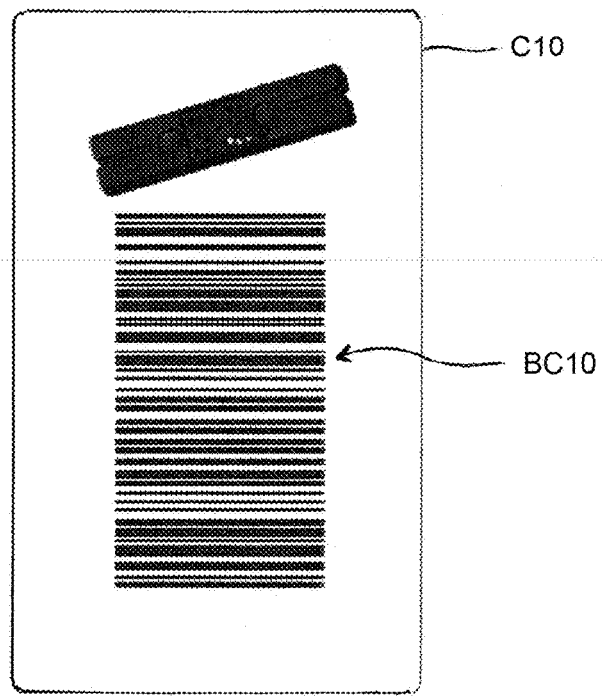
FIG. 14 illustrates an identification card comprising a bar code containing the reference features of the base.
Figure 15:
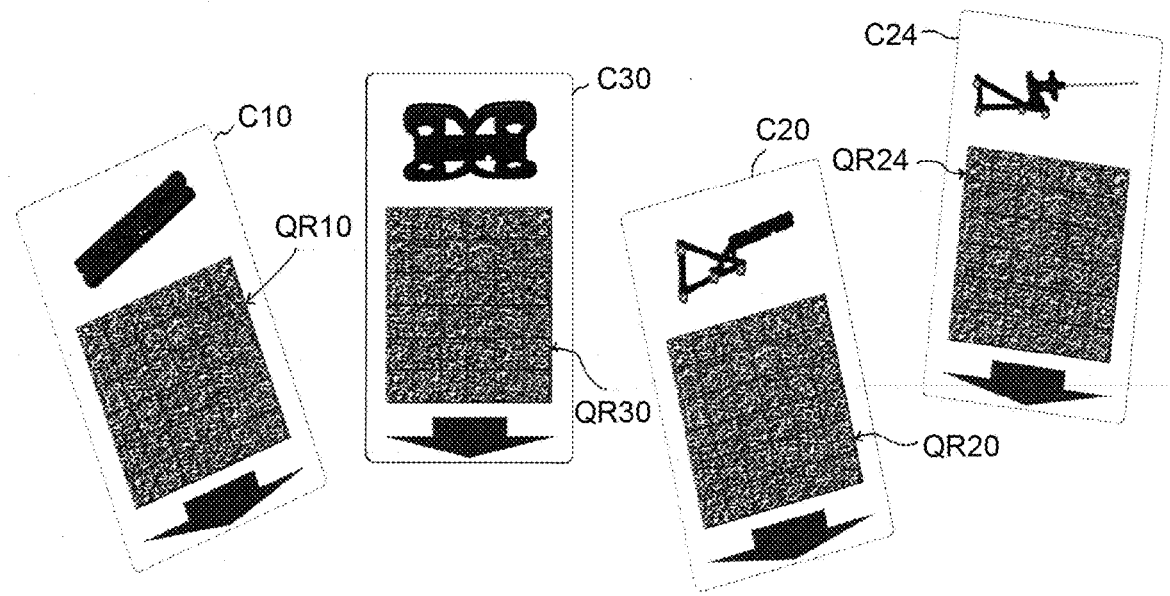
FIG. 15 illustrates identification cards comprising a datamatrix containing the reference features of the base, the registration phantom, the tracker and the tool.

In another embodiment, the reference features may be downloaded from another system which may be a storage device (i.e. external USB device) or a lecture device as barcode reader or datamatrix reader directly linked to the memory device or settled into the system. Advantageously, the datamatrix (i.e. QR code) contains all reference dimensions to be transferred into the system and may be printed onto a card format within the instrument package. This embodiment suits particularly the use of single-use instruments. It presents the advantage not to need software upgrade in case of modification of reference features. For example, FIG. 14 shows an identification card C10 for the base. In this embodiment, the reference features of the base are contained in a barcode BC printed onto the card. FIG. 15 shows identification cards C10, C30, C20 and C24 for the base, the registration phantom, the tracker and the tool respectively. The respective reference features of each of said components are contained in a datamatrix (respectively QR10, QR30, QR20 and QR24) printed onto the card. Thus, when a user wants to use a new component, he/she only has to read the barcode or datamatrix using a suitable reader in order to download the reference features of said component. Then, the computer uses said references features during implementation of the protocol.

The invention claimed is:

1. A modular fluoro-navigation instrument comprising:
    a base made of a substantially radiotransparent material, the base being configured to be secured to a patient's bone; and
    a tracker attachable to the base;
    wherein
    the modular fluoro-navigation instrument further comprises a registration phantom separate from the tracker and comprising a plurality of radiopaque fiducials;
    the base and the registration phantom comprise respective fixation members for reproducibly attaching the registration phantom to the base;
    the tracker comprises at least one fixation element cooperating with the fixation member of the base for reproducibly attaching the tracker to the base; and
    the at least one fixation element of the tracker, the fixation member of the registration phantom and the fixation member of the base are configured to cooperate according to at least two different engagement positions of the at least one fixation element of the tracker with the fixation member of the base and a single engagement position of the registration phantom with the fixation member of the base so as to provide at least two determined positions for the tracker with respect to the base and a unique position for the registration phantom with respect to the base.

2. The modular fluoro-navigation instrument according to claim 1, wherein the tracker is an optical tracker.

3. The modular fluoro-navigation instrument according to claim 1, wherein the tracker is an electromagnetic tracker.

4. The modular fluoro-navigation instrument according to claim 1, further comprising a deformable material configured to be placed between the patient's skin and a support surface of the base facing the patient's skin, wherein said deformable material is capable of fitting a shape of the patient's skin and of rigidifying under an external solicitation.

5. The modular fluoro-navigation instrument according to claim 1, further comprising an adhesive layer on a support surface of the base facing the patient's skin and configured to adhere to the patient's skin.

6. The modular fluoro-navigation instrument according to claim 1, wherein the base comprises a plurality of through holes.

7. The modular fluoro-navigation instrument according to claim 6, wherein at least two of said plurality of through holes have non-parallel orientations.

8. The modular fluoro-navigation instrument according to claim 6, further comprising a plurality of pins adapted to be inserted in the plurality of through holes of the base so as to secure percutaneously the base to the patient's bone.

9. The modular fluoro-navigation instrument according to claim 8, further comprising a fixation system for attaching each of said plurality of pins to the base.

10. The modular fluoro-navigation instrument according to claim 9, wherein said fixation system comprises at least one of:
- a threaded section of each of the plurality of pins cooperating with a respective threaded section of each of the plurality of through holes;
- an element slidable along each of the plurality of pins capable of forcibly engaging a corresponding housing in the base;
- a pressure screw;
- a clamp; and
- a wedge element.

11. The modular fluoro-navigation instrument according to claim 1, wherein the base comprises at least one slot configured to pre-position the base onto at least one of the plurality of pins previously implanted into the patient's bone.

12. The modular fluoro-navigation instrument according to claim 1, wherein the base comprises a plurality of bases having different sizes and/or shapes, the tracker comprises a single tracker and the registration phantom comprises a single registration phantom, wherein the single tracker and the single registration phantom are capable of being reproducibly attached to each of said plurality of bases.

13. The modular fluoro-navigation instrument according to claim 1, wherein the base comprises a single base, the tracker comprises a plurality of trackers and the registration phantom comprises a plurality of registration phantoms, wherein each of the plurality of trackers and each of the plurality of registration phantom is capable of being reproducibly attached to said single base.

14. A modular fluoro-navigation instrument comprising:
- a base made of a substantially radiotransparent material, the base being configured to be rigidly secured to a patient's bone; and
- a tracker rigidly attachable to the base;

wherein the modular fluoro-navigation instrument further comprises a registration phantom separate from the tracker and comprising a plurality of radiopaque fiducials;

the base and the registration phantom comprise respective fixation members for reproducibly attaching the registration phantom to the base;

the tracker comprises a fixation element cooperating with the fixation member of the base for reproducibly attaching the tracker to the base; and the base comprises a finger, the tracker includes a support comprising two passages arranged such that the finger engages one passage of the support when the tracker is fixed onto the base in a first position and the other passage of the support when the tracker is fixed onto the base in a second position, and the registration phantom comprises only one passage adapted to engage the finger when the registration phantom is fixed onto the base.

* * * * *